(12) United States Patent
Balschat et al.

(10) Patent No.: US 8,518,258 B2
(45) Date of Patent: Aug. 27, 2013

(54) HEMODIALYSIS DEVICE, HEMODIAFILTRATION DEVICE, METHOD FOR TAKING A SAMPLE IN CORRESPONDING DEVICES AND SAMPLING KIT FOR USE IN CORRESPONDING DEVICES AND METHOD

(75) Inventors: Klaus Balschat, Schwebheim (DE); Reiner Spickermann, Wasserlosen-Burghausen (DE); Josef Winter, Saarlouis (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 830 days.

(21) Appl. No.: 12/312,040

(22) PCT Filed: Oct. 22, 2007

(86) PCT No.: PCT/IB2007/004463
§ 371 (c)(1),
(2), (4) Date: Jan. 19, 2010

(87) PCT Pub. No.: WO2008/096202
PCT Pub. Date: Aug. 14, 2008

(65) Prior Publication Data
US 2010/0130906 A1    May 27, 2010

(30) Foreign Application Priority Data
Oct. 23, 2006   (DE) .......................... 10 2006 050 272

(51) Int. Cl.
*C02F 1/44* (2006.01)
*A61M 37/00* (2006.01)

(52) U.S. Cl.
USPC ......... 210/646; 604/4.01; 604/5.01; 604/6.15

(58) Field of Classification Search
USPC ............. 604/4.01, 5.01, 6.06, 6.1, 6.11, 6.15, 604/6.16; 210/645, 646
See application file for complete search history.

(56) References Cited

U.S. PATENT DOCUMENTS

| 4,634,430 A * | 1/1987 | Polaschegg .................. 604/141 |
| 4,770,769 A | 9/1988 | Schael |
| 5,630,935 A | 5/1997 | Treu |
| 5,725,773 A | 3/1998 | Polaschegg |
| 2003/0209475 A1 | 11/2003 | Connell et al. |
| 2006/0254982 A1 | 11/2006 | Kopperschmidt |

FOREIGN PATENT DOCUMENTS

| DE | 28 38 414 A1 | 3/1980 |
| DE | 28 38 414 C2 | 10/1984 |
| DE | 42 03 069 A1 | 8/1993 |
| DE | 103 36 539 A1 | 3/2005 |
| EP | 0 711 569 A1 | 5/1996 |
| EP | 1 595 560 A1 | 11/2005 |
| FR | 2 696 644 A1 | 4/1994 |
| GB | 2 110 564 A | 6/1983 |

* cited by examiner

*Primary Examiner* — Melanie Hand
(74) *Attorney, Agent, or Firm* — Jacobson Holman PLLC

(57) ABSTRACT

A hemodialysis machine or hemodiafiltration machine is provided that may be used directly for sampling for the connection to a hemodialyzer or for providing replacement fluid, as is required for regular microbiological testing. The machine does not require any additional components or any complex hygiene measures to prevent secondary contamination. By connecting an inventive sterile sampling set, samples can easily be taken. Closing elements and pumping mechanisms are controlled by a control unit as part of a sampling control program.

13 Claims, 1 Drawing Sheet

HEMODIALYSIS DEVICE, HEMODIAFILTRATION DEVICE, METHOD FOR TAKING A SAMPLE IN CORRESPONDING DEVICES AND SAMPLING KIT FOR USE IN CORRESPONDING DEVICES AND METHOD

This is a national stage of PCT/IB07/004463 filed Oct. 22, 2007 and published in German, which has a priority of German no. 10 2006 050 272.8 filed Oct. 23, 2006, hereby incorporated by reference.

BACKGROUND OF THE INVENTION

1. Field of the Invention

The invention relates to the field of machines for renal replacement therapy.

2. Description of the Related Art

In hemodialysis, blood is removed continuously from a patient in an extracorporeal circulation, passed through a hemodialyzer and reinfused back into the patient. In doing so, a mass exchange is performed, very similar to that taking place in the kidneys. The hemodialyzer consists of two chambers separated by a semipermeable membrane, one chamber of which has blood flowing through it while the other has a cleaning fluid—the dialysis fluid—flowing through it. For this purpose, commercial hemodialyzers usually have thousands of hollow fibers, the walls of which are semipermeable for the substances to be exchanged. Blood passes through the interior of the hollow fibers while dialysis fluid is fed into and removed from the fiber interspace, usually in the opposite direction.

Dialysis fluid contains blood constituents such as electrolytes in concentrations corresponding approximately to those of a healthy person, so that the corresponding concentrations in the blood can be kept at a normal level. Substances to be removed from the blood such as creatinine or urea are not present in the dialysis fluid, so they are removed from the blood by diffusion merely because of the concentration gradient on the membrane. With the help of a pressure gradient, excess water is withdrawn from the blood by convection and/or ultrafiltration.

To control such processes, hemodialysis machines are used to also ensure in most cases the preparation of the dialysis fluid from water and concentrates with the correct composition and temperature. In today's hemodiafiltration machines, this liquid is also used to compensate for the cleaning of blood (hemofiltration) brought about by increased convection. In hemodiafiltration, a larger amount of ultrafiltrate is withdrawn from the patient's blood during a hemodialysis treatment via the hemodialyzer and is replaced by replacement fluid up to the total amount of fluid to be withdrawn. With modern equipment, especially for treatment of chronic renal failure, the dialysis fluid prepared on-line during the treatment is used for this purpose by providing a line that branches off from the dialysis fluid circulation with one or more filter stages and by connecting it to the extracorporeal blood circulation upstream and/or downstream from the hemodialyzer.

The dialysis fluid itself is obtained from water and in most cases two concentrates which are mixed in a predetermined ratio by the hemodialysis machine. At the same time, the dialysis fluid is heated approximately to body temperature to perform the dialysis. The concentrates may be in liquid or dry form in smaller containers. In clinics and hospitals, the use of ring line systems with a central supply is also widespread.

The water and dialysis fluid must meet not only high requirements with regard to composition and temperature but also the microbiological purity is very important. To meet and ensure the required standards with regard to microbiological requirements (microbes, endotoxins), checking must be performed by sampling. Sampling is complicated because it is essential to prevent secondary contamination, which could falsify the microbiological tests.

To perform the sampling, so far additional components have been used. Sampling sites via self-closing septa, e.g., made of silicone, are widely used; these are installed in a line through which the flow passes. There are also T-shaped sampling sites for lengths of tubing that can be connected to a syringe without a needle. With all these approaches, it is essential that strict hygiene procedures be followed to prevent entrainment of secondary contamination through the sampling itself.

DE 103 36 539 A1 describes a T-shaped connecting piece for sampling fluids used in hemodialysis machines, in which the septum can be replaced easily. U.S. Pat. No. 5,630,935 describes a sampling valve for the water supply line of a hemodialysis machine.

DE 28 38 414 C2 describes a hemodialysis machine with which both fresh and spent dialysis fluid can be conveyed to a special sampling port with the help of the ultrafiltration pump. However, this requires additional lines and connections which must also be regularly included in the cleaning procedure.

The object of the invention is to improve upon a generic hemodialysis machine so that simple sampling of the prepared dialysis fluid is possible without any complex hygiene measures. The object of this invention is also to provide a corresponding method for sampling. Finally, another object of the invention is to provide simple sample containers for use with such a machine and such a method.

SUMMARY OF THE INVENTION

According to the teaching of the invention, this object is achieved by a hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting element, and further characterized in that the first and second connecting elements are couplings fitted for dialysis fluid connections according to DIN EN 1283.

According to the teaching of the invention, this object is also achieved by a hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting element, and further characterized in that the sampling control program for conveying the predetermined amount of dialysis fluid initially closes the first and second closing elements or keeps them closed and then opens the first closing element and operates the pumping mechanism for conveying the predetermined quantity of dialysis fluid into the sampling set connected to the first connecting element and then closes the first closing element again.

According to the teaching of the invention, this object is still further achieved by a hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting element, and further characterized in that it also has a bypass line that branches off from the dialysis fluid inlet line upstream from the first closing element and is provided with a third closing element and opens into the dialysis fluid outlet line downstream from the second closing element, whereby a fourth closing element is provided in the dialysis fluid outlet line downstream from the opening point.

The object of the present invention is also achieved by a hemodiafiltration machine, comprising a dialysis fluid circulation which has a source and a drain for dialysis fluid, a dialysis fluid inlet line leading from the source for dialysis fluid to a first connecting element, a dialysis fluid outlet line leading from the second connecting element to the drain for dialysis fluid, a substitute line branching off from the dialysis fluid inlet, line to a third connecting element, a pumping mechanism for circulating dialysis fluid in the dialysis fluid circulation and first closing element in the dialysis fluid inlet line and second closing element in the dialysis fluid outlet line and fifth closing element in the substitute line and also a control unit for triggering the pumping mechanism and the first closing element, the second closing element and the fifth closing element, whereby the first connecting element and the second connecting element are designed so that when performing a hemodiafiltration treatment, they are connected to the dialysis fluid chamber of a hemodialyzer that is divided by a semipermeable membrane into a dialysis fluid chamber and a blood chamber, so that dialysis fluid flows from the source through the dialysis fluid inlet line to the dialysis fluid chamber and from the dialysis fluid chamber to the drain via the dialysis fluid drain line, and the third connecting element is designed so that when performing a hemodiafiltration treatment, dialysis fluid is supplied as substitute to the patient's blood through a line connected to the third connecting element, characterized in that the control unit is designed so that it controls the first closing element, the second closing element and the fifth closing element as well as the pumping mechanism as part of a sampling control program that proceeds automatically in such a way that a predetermined amount of dialysis fluid is conveyed into a sampling set that is connected to the first connecting element, the second connecting element or the third connecting element.

Finally, the present invention also includes method for sampling dialysis fluid of a hemodiafiltration machine, comprising a dialysis fluid circulation which has a source and a drain for dialysis fluid, a dialysis fluid inline line leading from the source for dialysis fluid to a first connecting element, a dialysis fluid outlet line leading from a second connecting element to the drain for dialysis fluid, a substitute line branching off from the dialysis fluid inlet line to a third connecting element, a pumping mechanism for circulating dialysis fluid in the dialysis fluid in the dialysis fluid circulation and first closing element in the dialysis fluid inlet line and second closing element in the dialysis fluid outlet line and fifth closing element in the substitute line, whereby the first connecting element and the second connecting element are designed so that for performing a hemodiafiltration treatment, they are connected to the dialysis fluid chamber of a hemodialyzer that is divided by a semipermeable membrane into a dialysis fluid chamber and a blood chamber, so that dialysis fluid flows from the source through the dialysis fluid inlet line to the dialysis fluid chamber and from the dialysis fluid chamber through the dialysis fluid outlet line to the drain, and the third connecting element is designed so that dialysis fluid is supplied as substitute to a patient's blood through a line that is connected to the third connecting element when performing a hemodiafiltration treatment, characterized by the following method steps: closing the first closing element and the second closing element or short-circuiting the first connecting element and the second connecting element or keeping them closed, closing the fifth closing element or keeping them closed, connecting a sterile sampling set to the third connecting element, opening the fifth closing element, operating the pumping mechanism so that a predetermined amount of dialysis fluid flows into the sampling set, and closing the fifth closing element.

The invention is based on the observation that with a hemodialysis machine or hemodiafiltration machine, the connections that are already present for connecting the machine to a hemodialyzer or for providing replacement fluid directly may also be used for the sampling itself, because these connections are usually accessible directly for sampling prior to equipping them with the components of the extracorporeal blood circulation, most of which are disposable. These connections are regularly disinfected as part of the machine cleaning program and precisely the fluid whose samples are to be analyzed is flowing through these connections during a dialysis treatment. By connecting a fitting sterile sampling set, samples can easily be taken without requiring any special additional hygiene measures or running the risk of secondary contamination. On the equipment end, no modification is necessary except for setting up a special sampling control program in the control unit that is present anyway.

BRIEF DESCRIPTION OF THE DRAWINGS

Additional details and advantages of the invention are described in greater detail on the basis of an exemplary embodiment which is shown schematically in the drawings.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
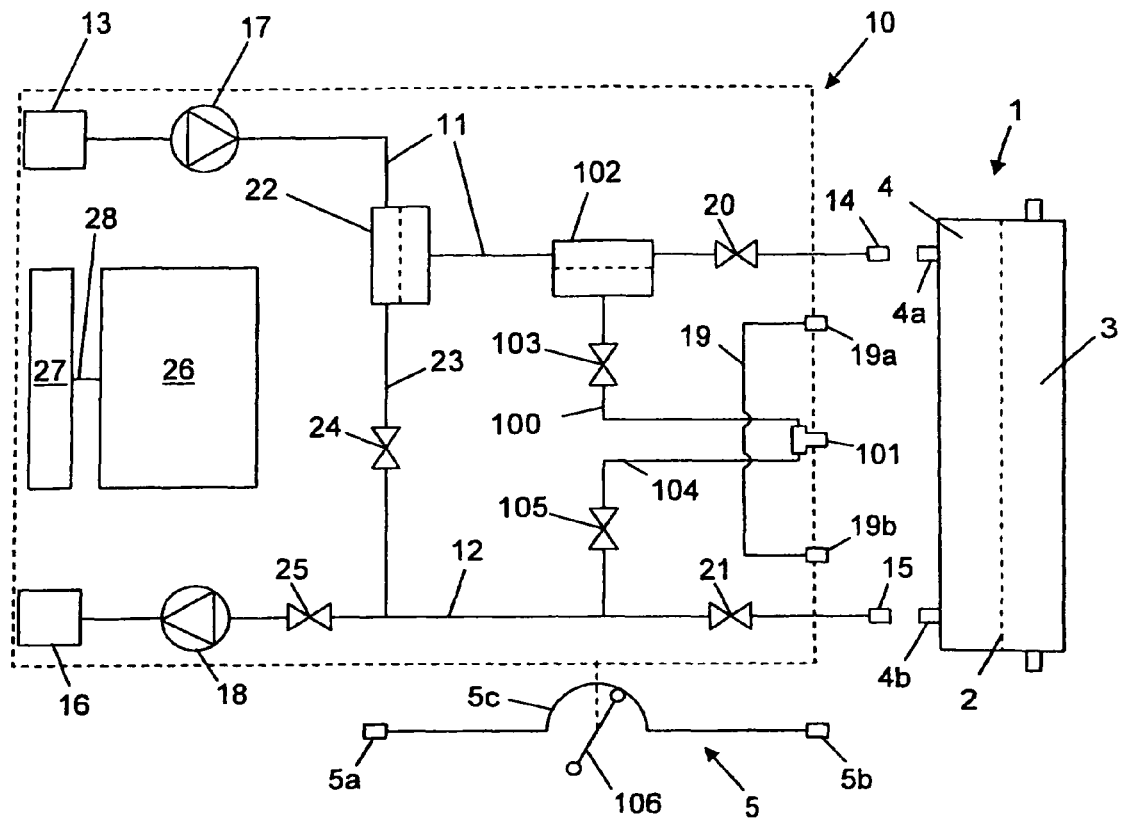
FIG. 1 shows an embodiment of an inventive hemodiafiltration machine.

With the help of FIG. 1, first the basic design of an inventive hemodialysis machine will be explained, where the operation of the hemodiafiltration machine 10, which is shown in FIG. 1, is limited to the treatment mode of hemodialysis. This is followed by a description of operation as an inventive hemodiafiltration machine.

Numerous possibilities are available to those skilled in the art for using actuators and sensors in a hemodialysis machine in general so that no details need be described here. The diagram in FIG. 1 is limited to a few of these elements which are sufficient to explain the present invention.

In hemodialysis, blood in an extracorporeal circulation is supplied to a hemodialyzer 1. In the hemodialyzer 1, a semipermeable membrane 2, usually designed in the form of multiple hollow fibers, separates a first chamber 3 (blood chamber), which is part of the extracorporeal blood circulation, from a second chamber 4 (dialysis fluid chamber) which is part of the dialysis fluid circulation. Substances to be removed from the blood pass through the semipermeable membrane 2 into the dialysis fluid and are removed in this way. At the same time, an excess of fluid can be ultrafiltered from the blood by ultrafiltration via a pressure gradient and removed through the dialysis fluid being discharged. Finally, an inverse diffusion gradient may also be used, e.g., for sodium ions, to transfer these substances from the dialysis fluid into the blood.

The blood chamber 3 can be connected by two connections 4a and 4b to a blood inlet line and a blood outlet line (not shown) while the dialysis fluid chamber 4 can be connected to the dialysis fluid inlet line 11 and the dialysis fluid outlet line 12 of the dialysis fluid circulation of the hemodialysis and/or hemodiafiltration machine 10. The dialysis fluid inlet line 11 leads from a dialysis fluid source 13 to a first connecting means 14 for connection to the first connection 4a of the dialysis fluid chamber 4 while the dialysis fluid outlet line 12 leads from a second connecting means 15 to the connection with the second connection 4b of the dialysis fluid chamber 4 to a drain 16. A first pump mechanism 17 is provided in the dialysis fluid inlet line 11 and a second pump mechanism 18 is provided in the dialysis fluid outlet line 12 for circulating the dialysis fluid and for controlling the withdrawal of fluid during a dialysis treatment. The two pump mechanisms 17 and 18 as well as the source 13 and the drain 16 are indicated only schematically in FIG. 1. Those skilled in the art will be aware of numerous approaches for implementation thereof, whereby the pump mechanisms are to be interpreted in a broad sense. They may be used as separate pumps that are actively pumping, but it is equally possible to use a so-called balance chamber system with a separate ultrafiltration line, such as that distributed by the patent applicant and described in DE 28 38 414 C2, the disclosure content of which is herewith explicitly cited.

The connections 4 and 4b are designed according to DIN EN 1283 in commercial hemodialyzers, whereby the first and second connecting means 14 and 15 are complementary accordingly and are usually designed in the form of so-called Hansen couplings. If a hemodialyzer 1 is not connected to the hemodialysis machine 10, the two connecting means 14 and 15, which are connected to the housing of the hemodialysis machine by a flexible length of tubing on this end of the dialysis fluid inlet line 11 and the dialysis fluid outlet line 12, are short-circuited with the connections 19a and 19b via a short-circuit piece 19 which is integrated into the machine. In this way, the complete dialysis fluid circulation can be flushed and cleaned with a cleaning fluid in a cleaning operation between individual blood treatments without resulting in dead space. Only the hemodialyzer is usually discarded after a treatment. Between the blood treatments the dialysis fluid circulation remains essentially in this short-circuited state.

A first closing means 20 designed as a switching valve is provided in the dialysis fluid inlet line 11 and a similar second closing means 21 is provided in the dialysis fluid outlet line. The flow in these lines can be interrupted and/or enabled with the first and second closing means 20 and 21.

A first sterile filter 22 may be provided in the dialysis fluid inlet line 11 to additionally filter fresh dialysis fluid before introducing it into the hemodialyzer. To increase the lifetime of the filter and reduce the risk of rupture and thus entrainment of microorganisms deposited in the filter, the filter can usually be flushable through a bypass line 23 which is usually present anyway in hemodialysis machines, as illustrated in FIG. 1, said bypass line connecting the dialysis fluid inlet line 11 to the dialysis fluid outlet line 12. To activate the bypass, a third closing means 24 is connected to the bypass line 23.

Especially in the event of an error, the bypass line 23 allows a safe state to be achieved during a hemodialysis treatment. In this case, the first and second closing means 20 and 21 are closed and the third closing means 24 is opened. The hemodialysis machine 10 may continue the processing and discarding of dialysate on a continuous basis, which facilitates continuation of the treatment after elimination of the error.

Downstream from the opening of the bypass line 23 into the dialysis fluid outlet line 12, a fourth closing means 25 may be provided.

The hemodialysis machine 10 is controlled and monitored by a control unit 26. To do so, the control unit 26 is connected to signal lines the individual actuators and sensors of the device, although they are not shown in FIG. 1 for the sake of simplicity.

If the hemodialysis machine 10 is also to be used for processing replacement fluid and thus as a hemodiafiltration unit, a substituate line 100 branches off from the dialysis fluid inlet line 11, leading to a third connecting means 101. In the embodiment depicted in FIG. 1, the branching can be accomplished by a second sterile filter 102, with dialysis fluid flowing through the first chamber thereof during the treatment, so that it is being flushed constantly. A fifth closing means 103 is connected to the substituate line 100 branching away from the second chamber of the second sterile filter 102. To design the substituate line 100 to be flushable, a flushing line 104 leading from the third connecting means 101 to the dialysis fluid outlet line 12 may be provided, with a sixth closing means 105 optionally being installed in this flushing line. In this case, the third connecting means 101 are designed as a T-piece to allow a connection of the substituate line 100 to the extracorporeal circulation.

For the blood treatment, a line segment 5 designed as a disposable part with a complementary connection piece 5a would be connected to the third connecting means 101. The other line end 5b, if not already integrally connected to the extracorporeal circulation, is then connected to the extracorporeal circulation at a suitable location due to the design thereof. A pump segment 5c for insertion into a pump 106 of the hemodiafiltration machine 10 designed as a roller pump may be provided in the line segment 5.

The control unit 26 is connected to an input and output unit 27 via a data line 28. The input and output unit 27 comprises means for activating a special sampling control program in the control unit 26.

Figure 2:
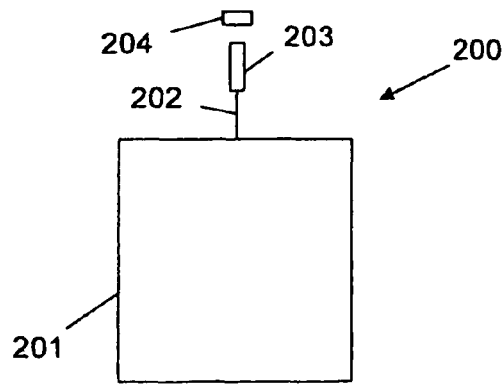
FIG. 2 shows an embodiment of an inventive sampling set.

To perform the inventive method for sampling, at first only a sterile sampling set is connected to the first, second or third connecting means 14, 15 or 101. FIG. 2 shows an exemplary embodiment of such a set. The sterile sampling set 200 consists of a container means 201, preferably designed as a bag, which leads to a container connecting means 203 via a line segment 202. In addition, a container closing means designed as a hose clamp may be provided in the line segment 202 or at a suitable location so that the sampling set can be closed after sampling. A sterile closing cap 204 which may be supplied as part of the sterile sampling set 200 is also suitable as the container closing means. By closing off the container connecting means 203 with the closing cap 204 after sampling, it is possible to ensure that the sample fluid is not contaminated on route to the analytical laboratory.

If the sampling set 200 is to be connected to the first or second connecting means 14 or 15, then the container connecting means 203 is designed as a connecting port according to DIN EN 1283 like the connection 4a, 4b of the hemodialyzer 1. In the case of a connection to the third connecting means 101, it is designed to be complementary to this connecting means accordingly, whereby different types of connectors are used, depending on the manufacturer. The inventive sampling set is especially versatile if the container connecting means 203 is already equipped with both forms of connections, e.g., in the form of a Y piece. It is also possible to provide for compatibility with both types of connections to be established by means of a removable adapter piece.

The sampling set 200 is in a sterile form to prevent secondary contamination. To do so it may be sufficient for the inside surfaces to be sterile if it is possible to rule out any contamination by externally accessible surfaces. However, the sampling set is expediently completely sterilized in repackaging and then distributed in the repackaged form.

In addition to the embodiment as a bag, other design options are also possible. For example, a sterile syringe with corresponding connecting means may also be used.

Before the sampling set is connected to the hemodiafiltration machine 10, the operator selects a special sampling control program via appropriate input means of the input and output unit 27. Within the context of this program, which takes place automatically in the control unit 26, alternative method steps may also take place, as described below.

In the case of a connection to the first or second connecting means, the program at first closes the first and second closing means 20 and 21 or keeps them closed if they are already closed. The operator is then instructed to connect the sampling set via the input and output unit 27. After connecting the sampling set 200 to the first or second connecting means, the operator confirms the connection to the input and output unit 27; if necessary, there is also a selection of the connection used. The control program in the control unit 26 then opens the predetermined or selected first or second closing means 20 or 21 to which the sampling set is connected and activates the pumping mechanism 17 so that a predetermined amount of dialysis fluid can flow into the container 201. Then the opened first or second closing means 20 or 21 is closed again. The conclusion of the sampling control program is displayed on the input and output unit 27. The sampling set may then be removed.

In another embodiment of the invention, it is possible for the hemodiafiltration machine to automatically make available a labeling printout, which can be applied to the sampling set and already contains the required information such as the equipment number and the time of sampling.

The sampling control program may use various valve switching operations for sampling, depending on the design of the hemodiafiltration machine. In the case of the machine illustrated in FIG. 1, all the closing means may be closed in connection to the first connecting means 14 and only the first closing means 20 need be opened for sampling. In the case of a connection to the second connecting means 15, however, in addition to the opening of the second closing means 21, opening of a closing means in a line connecting the dialysis fluid inlet line 11 to the dialysis fluid outlet line 12 to be opened is also required. In the embodiment shown in FIG. 1, the bypass line 23 may be used for this purpose when opening the third closing means 24 or the substituate line 100 and the flushing line 104 with opening of the fifth and sixth closing means 103 and 105. The fourth closing means 25 is expediently closed.

In connection to the third closing means 101, the first and second closing means 20 and 21 may also be opened in the case of short circuit of the first and second connecting means 14 and 15. To this end, sensors may be provided on the connections 19a and 19b of the short-circuit piece 19, these sensors being able to detect the presence of the connection in general. For sampling, the fifth closing means 103 or the third and sixth closing means 24 and 105 are opened.

Regardless of the alternatives implemented, the corresponding input and output routines of the input and output unit 27 may also permit central activation of the sampling program in the manner already described as well as operation of the individual method steps and optionally the selection of a certain fluid course and/or connecting means by the user, so that implementation of the inventive method with the help of the inventive hemodialysis or hemodiafiltration machine is designed to be especially user friendly.

The present invention permits simple sampling of dialysis fluid prepared by the hemodialysis or hemodiafiltration machine and ready-to-use dialysis fluid without requiring the installation of any additional components or maintaining complex hygiene measures. At the same time, secondary contamination is effectively prevented. The sampling set, which is also inventive, may be manufactured inexpensively in large numbers as a sterile plastic item. Due to the connection compatibility of the sampling set with the existing connections for the ready-to-use dialysis fluid, this meets a long-standing need for a simple and hygienically trouble-free option of routine sampling for microbiological tests.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting element, and further characterized in that the first and second connecting elements are couplings fitted for dialysis fluid connections according to DIN EN 1283.

2. A hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting elements, and further characterized in that the sampling control program for conveying the predetermined amount of dialysis fluid initially closes the first and second closing elements or keeps them closed and then opens the first closing element and operates the pumping mechanism for conveying the predetermined quantity of dialysis fluid into the sampling set connected to the first connecting element and then closes the first closing element again.

3. A hemodialysis machine having a dialysis fluid circulation which has a source and a drain for dialysis fluid, a dialysis fluid inlet line leading from the source for dialysis fluid to a first connecting element, a dialysis fluid outlet line leading from a second connecting element to the drain for dialysis fluid, a pumping mechanism for circulating dialysis fluid in the dialysis fluid circulation and first closing element in the dialysis fluid inlet line and second closing element in the dialysis fluid outlet line and also a control unit for controlling the pumping mechanism and the first and second closing elements, whereby the first and second connecting elements are designed so that they are connected to the dialysis fluid chamber of a hemodialyzer that is divided by a semipermeable membrane into a dialysis fluid chamber and a blood chamber when performing a hemodialysis treatment, so that dialysis fluid flows from the source through the dialysis fluid inlet line to the dialysis fluid chamber and from the dialysis fluid chamber to the drain via the dialysis fluid outlet line, characterized in that the control unit is designed so that it controls the first and second closing elements and the pumping mechanism as part of a sampling control program that runs automatically, so that a predetermined amount of dialysis fluid is conveyed into a sampling set that is connected to the first or second connecting elements, and further characterized in that it also has a bypass line that branches off from the dialysis fluid inlet line upstream from the first closing element and is provided with a third closing element and opens into the dialysis fluid outlet line downstream from the second closing element, whereby a fourth closing element is provided in the dialysis fluid outlet line downstream from the opening point.

4. The hemodialysis machine according to claim 3, characterized in that the sampling control program initially closes the first closing element, the second closing element and the fourth closing element or keeps them closed for conveyance of the predetermined amount of dialysis fluid and then opens the third closing element or holds them open and opens the second closing element and then operates the pumping mechanism for conveying the predetermined amount of dialysis fluid into the sampling set connected to the second closing element and then closes the second closing element again.

5. The hemodiafiltration machine, comprising a dialysis fluid circulation which has a source and a drain for dialysis fluid, a dialysis fluid inlet line leading from the source for dialysis fluid to a first connecting element, a dialysis fluid outlet line leading from the second connecting element to the drain for dialysis fluid, a substituate line branching off from the dialysis fluid inlet, line to a third connecting element, a pumping mechanism for circulating dialysis fluid in the dialysis fluid circulation and first closing element in the dialysis fluid inlet line and second closing element in the dialysis fluid outlet line and fifth closing element in the substituate line and also a control unit for triggering the pumping mechanism and the first closing element, the second closing element and the fifth closing element, whereby the first connecting element and the second connecting element are designed so that when performing a hemodiafiltration treatment, they are connected to the dialysis fluid chamber of a hemodialyzer that is divided by a semipermeable membrane into a dialysis fluid chamber and a blood chamber, so that dialysis fluid flows from the source through the dialysis fluid inlet line to the dialysis fluid chamber and from the dialysis fluid chamber to the drain via the dialysis fluid drain line, and the third connecting element is designed so that when performing a hemodiafiltration treatment, dialysis fluid is supplied as substitute to the patient's blood through a line connected to the third connecting element, characterized in that the control unit is designed so that it controls the first closing element, the second closing element and the fifth closing element as well as the pumping mechanism as part of a sampling control program that proceeds automatically in such a way that a predetermined amount of dialysis fluid is conveyed into a sampling set that is connected to the first connecting element, the second connecting element or the third connecting element.

6. The hemodiafiltration machine according to claim 5, characterized in that the first connecting element and the second connecting element are couplings suitable for dialysis fluid connections according to DIN EN 1283.

7. The hemodiafiltration machine according to claim 5, characterized in that the sampling control program for conveying the predetermined amount of dialysis fluid initially closes the first closing element, the second closing element and the fifth closing element or keeps them closed, and then opens the fifth closing element and then operates the pumping mechanism for delivering the predetermined amount of dialysis fluid into the sampling set connected to the third connecting element and then closes the fifth closing element again.

8. The hemodiafiltration machine according to claim 5, characterized in that the sampling control program for delivering the predetermined amount of dialysis fluid at first closes the first closing element, the second closing element and the fifth closing element or keeps them closed and then opens the first closing element and operates the pumping mechanism for delivering the predetermined amount of dialysis fluid into the sampling set connected to the first connecting element and then closes the first closing element again.

9. The hemodiafiltration machine according to claim 5, characterized in that it also has a bypass line branching off from the dialysis fluid inlet line upstream from the first closing element, said bypass line being equipped with a third closing element and opening into the dialysis fluid outlet line downstream from the second closing element whereby a fourth closing element is provided in the dialysis fluid outlet line downstream from the opening point.

10. The hemodiafiltration machine according to claim 9, characterized in that the sampling control program for conveying the predetermined amount of dialysis fluid at first closes the first closing element, the second closing element, the fourth closing element and the fifth closing element or keeps them closed and then opens the third closing element or keeps them open and opens the second closing element and then operates the pumping mechanism for conveying the predetermined amount of dialysis fluid into the sampling set connected to the second connecting element and then closes the second closing element again.

11. The hemodiafiltration machine according to claim 5, characterized in that the third connecting element are sealed with a cover and the inside surfaces of the third connecting element that come in contact with fluid can be cleaned via the branching substituate line and a flushing line leading away from the third connecting element in continuous flow.

12. The hemodiafiltration machine according to claim 11, characterized in that the flushing line opens into the dialysis fluid outlet line downstream from the second closing element and is equipped with a sixth closing element.

13. The method for sampling dialysis fluid of a hemodiafiltration machine, comprising a dialysis fluid circulation which has a source and a drain for dialysis fluid, a dialysis fluid inline line leading from the source for dialysis fluid to a first connecting element, a dialysis fluid outlet line leading from a second connecting element to the drain for dialysis fluid, a substituate line branching off from the dialysis fluid inlet line to a third connecting element, a pumping mechanism for circulating dialysis fluid in the dialysis fluid in the dialysis fluid circulation and first closing element in the dialysis fluid inlet line and second closing element in the dialysis fluid outlet line and fifth closing element in the substituate line, whereby the first connecting element and the second connecting element are designed so that for performing a hemodiafiltration treatment, they are connected to the dialysis fluid chamber hemodialyzer that is divided by a semipermeable membrane into a dialysis fluid chamber and a blood chamber, so that dialysis fluid flows from the source through the dialysis fluid inlet line to the dialysis fluid chamber and from the dialysis fluid chamber through the dialysis fluid outlet line to the drain, and the third connecting element is designed so that dialysis fluid is supplied as substituate to a patient's blood through a line that is connected to the third connecting element when performing a hemodiafiltration treatment, characterized by the following method steps: closing the first closing element and the second closing element or short-circuiting the first connecting element and the second connecting element or keeping them closed, closing the fifth closing element or keeping them closed, connecting a sterile sampling set to the third connecting element opening the fifth closing element, operating the pumping mechanism so that a predetermined amount of dialysis fluid flows into the sampling set, and closing the fifth closing element.

\* \* \* \* \*

UNITED STATES PATENT AND TRADEMARK OFFICE
CERTIFICATE OF CORRECTION

PATENT NO.       : 8,518,258 B2  
APPLICATION NO. : 12/312040  
DATED            : August 27, 2013  
INVENTOR(S)      : Balschat et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1100 days.

Signed and Sealed this

Fifteenth Day of September, 2015

Michelle K. Lee
*Director of the United States Patent and Trademark Office*